(12) United States Patent
Fernando

(10) Patent No.: US 6,432,717 B1
(45) Date of Patent: Aug. 13, 2002

(54) STABILIZED TEST COMPOSITION, DEVICE AND METHOD FOR THE DETERMINATION OF CYANURIC ACID IN WATER

(75) Inventor: Sellapperumage Rupasiri Fernando, Granger, IN (US)

(73) Assignee: Environmental Tests Systems, Inc., Elkhart, IN (US)

( * ) Notice: Subject to any disclaimer, the term of this patent is extended or adjusted under 35 U.S.C. 154(b) by 28 days.

(21) Appl. No.: 09/629,346

(22) Filed: Aug. 1, 2000

(51) Int. Cl.⁷ .................................................. G01N 33/00
(52) U.S. Cl. ........................................ 436/106; 436/111
(58) Field of Search ................... 436/106, 111

(56) References Cited

U.S. PATENT DOCUMENTS

| | | | |
|---|---|---|---|
| 4,039,284 A | | 8/1977 | Mancini |
| 4,057,525 A | * | 11/1977 | Kikuchi et al. ............ 524/386 |
| 4,189,395 A | * | 2/1980 | Bland ...................... 15/104.93 |
| 4,255,301 A | * | 3/1981 | Minagawa et al. ......... 524/280 |
| 4,855,239 A | | 8/1989 | Rupe |

OTHER PUBLICATIONS

Venable et al., "Cyanuric Acid As An Oxidation Product of Uric Acid. Its Probable Identity With Tetracarbonimide", *J. Am. Chem. Soc.*, vol. 39, pp. 1750–1755 (1917).

C. J. Downes et al., "Determination of Cyanuric Acid Levels in Swimming Pool Waters by u.v. Absorbance, HPLC and Melamine Cyanurate Precipitation", *Water Res.*, vol. 18, No. 3, pp. 277–280, (1984).

* cited by examiner

*Primary Examiner*—Jill Warden
*Assistant Examiner*—Yelena G. Gakh
(74) *Attorney, Agent, or Firm*—Barnes & Thornburg

(57) ABSTRACT

A test reagent composition and device are provided for determination of cyanuric acid in water, said composition including melamine, a pH indicator that changes color due to the reaction of melamine with the cyanuric acid in the water, and a stabilizing compound capable of forming hydrogen bonds with the melamine but which does not compete with the cyanuric acid.

16 Claims, No Drawings

STABILIZED TEST COMPOSITION, DEVICE AND METHOD FOR THE DETERMINATION OF CYANURIC ACID IN WATER

FIELD OF THE INVENTION

The present invention relates to an improved test reagent composition for colorimetrically determining the quantity of cyanuric acid in water. More particularly, the invention relates to a stabilized test composition which can be incorporated into a matrix such as paper which when contacted with an aqueous fluid containing cyanuric acid will result in the formation of a color which is proportional to the quantity of cyanuric acid present. Such test devices have been shown to exhibit prolonged thermal and shelf stability.

BACKGROUND OF THE INVENTION

As the number of swimming pools and spas increase around the world, the need for effective tools to monitor and control pool water chemistry and especially sanitizer levels becomes more and more important. This is especially true in pools used by the public where the bather concentration is high and the threat of contagious disease is always present. In order to control the harmful microorganism population of pools it has been found over the years that chlorine is the most effective and economical sanitizer. However, as popular as chlorine is, it nevertheless has certain drawbacks, which must be considered in maintaining a well-managed swimming pool or spa. One particularly serious problem associated with the use of chlorine as a sanitizer in outdoor pools is that it tends to be destroyed by sunlight.

In this regard it has been found that the addition of cyanuric acid (2,4,6-trihydroxy-1,3,5-triazine) to the outdoor pool water can be effective as an extender or stabilizer for chlorine. However, the concentration of cyanuric acid must be rather carefully adjusted since too little obviously is ineffective as a stabilizer for the chlorine while too much can dramatically slow down the rate at which microorganisms are destroyed by the chlorine. It has been found that the most effective concentration of cyanuric acid in a swimming pool or other recreational water lies between approximately 30 and 100 parts per million (ppm) with an ideal range of about from 30 to 50 ppm and a maximum concentration of about 150 ppm of cyanuric acid.

Accordingly, in order to maintain the effectiveness of the cyanuric acid in the swimming pool, it is necessary to measure the concentration thereof using a test device or concentration measuring system. One current test commonly used in the swimming pool industry involves the melamine turbidimetric methodology. In this scheme, melamine is added to a sample of the pool water, which in the presence of cyanuric acid causes the formation of a finely dispersed precipitate. The turbidity created by this precipitate formation is proportional to the amount of cyanuric acid present. By measuring this turbidity using visual or instrumental methods, an estimation of the concentration of cyanuric acid can be obtained. This test however is not completely acceptable since turbidimetric methods tend in general to be unreliable in that other factors can cause turbidity and precipitates are obviously less homogenous than solutions.

For this reason, attempts have been made over the years to replace the turbidimetric analytical procedures with calorimetric methodologies. More recently, calorimetric reagent strip methods have been developed which offer simplicity and exactness in measuring cyanuric acid. Such methods and devices involve the use of melamine and an indicator incorporated into a matrix material such as paper that when contacted with the pool or spa water changes color in proportion to the amount or concentration of cyanuric acid present therein. These test devices, however, commonly suffer from a lack of thermal and shelf stability which hampers the commercialization of the devices and at times result in inaccurate analytical measurements.

DESCRIPTION OF THE PRIOR ART

U.S. Pat. No. 4,855,239 discloses and claims the use of melamine and an indicator material, that is preferably incorporated into a paper matrix resulting in a utilitarian test strip device. This test device commonly suffers from the aforementioned stability problems.

U.S. Pat. No. 4,039,284 discloses and claims a formulation for the calorimetric determination of cyanuric acid comprising a thymolsulfonphthalein compound, monoethanolamine and a stilbene compound. Regardless of its suggested efficacy, it appears that there are no commercially available products based on this technology.

Aside from the above patents, very little literature exists relative to the interaction of cyanuric acid with other compounds to form colored compounds. Veneable, C. and Moore, F.; J. Am. Chem. Soc. 39, 1750, 1917 disclose that cyanuric acid will react with certain metals such as copper to produce colored compounds; however, the reaction must take place under severe alkaline conditions and heat which conditions obviously are not amenable to a field test system.

All other prior art literature relates to colorless turbidimetric reactions between cyanuric acid and other compounds which art has no relevance here.

SUMMARY OF THE INVENTION

It has now been found that by using melamine, an appropriate pH indicator material, a buffer system and at least one melamine stabilizing compound in a test reagent composition, a test system substantially stabilized against thermal degradation can be prepared. The basic stabilizing system comprises the use of one or more compounds that form hydrogen bonds with the melamine but do not compete with the reaction between the melamine and the cyanuric acid in the test fluid.

DESCRIPTION OF THE PREFERRED EMBODIMENTS

As stated in U.S. Pat. No. 4,855,239, the basic colorimetric test system for determining cyanuric acid in water, and especially swimming pool and spa water, comprises using a combination of melamine and a pH responsive indicator material along with an appropriate buffer system. By carefully adjusting the pH of the test composition to within a designated range with the buffer system, a simple to use and effective calorimetric cyanuric acid test system can be devised. When this reagent composition is contacted with a test sample containing cyanuric acid, a shift in the pH of the test system results which in effect creates a color change which is proportional to the amount of cyanuric acid in the fluid being tested. Such test systems have been found to be notoriously unstable and difficult to manufacture.

Although U.S. Pat. No. 4,855,239 suggests two slightly different approaches to adjusting the pH of the test composition to achieve a useful product, it has been found in the present invention that optimum results are achieved if, using a suitable state of the art buffer system, the composition is adjusted to within a pH range of about from 6.4 to 8.0 with a range of about from 6.9 to 7.1 being preferable. When such an adjustment is achieved, the melamine contacting the cyanuic acid results in a significant color change proportion to and indicative of the amount of cyanuric acid present in the fluid being tested.

It should also be noted here that the use of melamine in a cyanuric acid test system usually creates a precipitate that could possibly interfere with the readout mechanism when a liquid calorimetric system is being employed. Although the melamine/cyanuric acid precipitate can be removed to more easily and accurately determine the color produced when the composition is used as a liquid format or other means can be employed to read the color formed, it is preferable to incorporate the composition in a solid state matrix such as paper. In this solid state or dry format test device the interference due to the melamine/cyanuric acid precipitate is usually eliminated.

In preparing the compositions of the present invention, consideration must be given to the selection of indicator materials and the concentration of melamine in the test composition. Indicators such as methyl red, phenol red, thymol blue, bromthymol blue, cresol red, metacresol purple, neutral red, curcumin, pyrocatecol violet and mixtures thereof may be selected as color forming agents.

The concentration of melamine (cyanurotriamide) in the reagent mixture should be set at from about 0.04 g/100 ml to about 0.5 g/100 ml. Moreover, the melamine concentration must be set to be in excess of the anticipated concentration of cyanuric acid being detected but must not be such that the pH change caused by contact of the reagent composition with the cyanuric acid is hindered.

As previously noted, it is preferable to incorporate the reagent composition into a solid state matrix so that the formation of a precipitate does not hinder in the estimation of the color change. Examples of matrix materials which can be utilized are filter paper, glass fibers, cellulosic materials, synthetic fibers, polymers, particulate inorganic materials, and so forth. The matrix must however be impervious to and not react with the fluid being tested and must be reasonably hydrophilic and porous so that the fluid being tested wets the matrix and the analyte contained therein reacts with the incorporated reagent composition.

A particularly advantageous use of the dry or solid state test devices described next above is in conjunction with an instrumental read out means. This can be accomplished by using a reflectance color measuring device wherein the color of the reagent matrix is measured and interpreted to give a readout in concentration of cyanuric acid in the fluid being tested.

Referring now to the stabilizing compound used in the present invention, this ingredient is a compound that forms hydrogen bonds with the melamine and accordingly stabilizes the N—H groups thereof from air oxidation and does not compete with the reaction between melamine and cyanuric acid. Such materials are preferably compounds containing alcohol or ketone groups and can be used individually or as mixtures that are added to the reagent composition. Examples of such compounds are the following: polyethylene glycol (PEG), ethylene glycol, glycerol, phenylarsine oxide (PAO), and N-tris(hydroxymethyl)methyl-2-aminoethanesulfonic acid (TES).

These materials are usually added directly to the test composition and the concentration of the materials used is related to the effectiveness of the individual compound and the desired stability versus the cost of the material. As stated above, such materials may involve the use of an individual stabilizer or may involve mixing several stabilizers to form a cocktail that will achieve the desired stability and reactivity.

EXAMPLES

The following Examples are illustrative of the present invention:

Example 1

This example represents an unstabilized reagent test composition.

| | |
|---|---|
| Deionized Water | 100.0 ml. |
| Polystyrene Sulfonic Acid (Na Salt) | 0.3 g. |
| Melamine | 0.18 g. |
| Sodium Chloride | 1.0 g. |
| Thymol Blue | 0.004 g. |
| Cresol Red | 0.03 g. |

The polystyrene sulfonic acid salt was dissolved in the deionized water with stirring. The melamine was added and the stirring continued until the melamine dissolved. Then the sodium chloride, thymol blue and cresol red were added and the mixture stirred until all ingredients were dissolved. The pH of the solution was then adjusted to 7.0 with HCl.

S & S 903 filter paper was then dipped into the reagent solution and dried in a hot air tunnel. The resulting dried paper was bright yellow in color.

Standard solutions of cyanuric acid in swimming pool water were prepared and the following colors obtained by immersing the reagent paper into such standard solutions and immediately removing the paper from the water:

| Cyanuric Acid Conc. (ppm) | Color |
|---|---|
| 0 | Yellow |
| 40 | Orange |
| 100 | Magenta |
| 150 | Purple |

A quantity of the same reagent strip test devices were placed in a closed container with desiccant and subjected to heat stress at 60 degrees centigrade for three weeks. They were then tested as described above and found to give the following results:

| Cyanuric Acid Conc. (ppm) | Color |
|---|---|
| 0 | Pale Yellow |
| 40 | Yellow |
| 100 | Orange |
| 150 | Magenta |

As can be seen from the above data, the thermal stress resulted in a test device which gave erroneous results.

Example 2

Test devices were prepared using the same procedures and formulation as described in Example 1 next above, except that 0.13 g. of glycerol and 0.5 g. of polyethylene glycol were added to the impregnating solution. After subjecting the devices to the same accelerated thermal stability tests as described in Example 1 the stressed test devices gave the same results as the unstressed devices.

What is claimed is:

1. A test reagent composition for the determination of cyanuric acid in water, said composition including melamine and a pH indicator material which changes color due to the reaction of melamine with the cyanuric acid in the water, the improvement which comprises the addition to the composition of at least one stabilizing compound capable of forming hydrogen bonds with the melamine but does not compete with the reaction of the melamine with the cyanuric acid resulting in a stabilized test composition.

2. A test reagent composition as in claim 1 wherein the stabilizer compound is selected from the group consisting of polyethylene glycol, ethylene glycol, glycerol, phenylarsene oxide, N-tris(hydroxymethyl)methyl-2-aminoethanesulfonic acid and mixtures thereof.

3. A test reagent composition as in claim 1 which additionally comprises a buffer system for maintaining the pH of the composition within a range of about from 6.4 to 8.0.

4. A test reagent composition as in claim 1 which additionally comprises a buffer system for maintaining the pH of the composition within a range of about from 6.9 to 7.1.

5. A test reagent composition as in claim 1 wherein the indicator is selected from the group consisting of methyl red, phenol red, thymol blue, bromthymol blue, cresol red, metacresol purple, neutral red, curcumin, pyrocatecol violet and mixtures thereof.

6. A test device for determining the amount of cyanuric acid in water comprising the dried residue of a test reagent composition consisting essentially of melamine and an indicator which changes color in response to a change in the pH of the environment in the matrix when the matrix is contacted with an aqueous solution of cyanuric acid, the improvement which comprises the inclusion of at least one stabilizing compound capable of forming hydrogen bonds with the melamine but which compound does not compete with the cyanuric acid.

7. A test device as in claim 6 wherein the stabilizing compound is selected from the group consisting of polyethylene glycol, ethylene glycol, glycerol, phenylarsene oxide, N-tris(hydroxymethyl)methyl-2-aminoethanesulfonic acid and mixtures thereof.

8. A test device as in claim 6 wherein the test reagent composition additionally comprises a buffer system for maintaining the device within a pH range of about from 6.4 to 8.0.

9. A test device as in claim 6 wherein the test reagent composition additionally comprises a buffer system for maintaining the device within a pH range of about from 6.9 to 7.1.

10. A test device as in claim 6 wherein the pH indicator is selected from the group consisting of methyl red, phenol red, thymol blue, cresol red, metacresol purple, neutral red, curcumin, pyrocatecol violet and mixtures thereof.

11. A test method for the determination of cyanuric acid in water comprising:

A. contacting a sample of the water with a test reagent system comprising melamine, a pH indicator material which changes color due to a reaction of melamine with cyanuric acid, a buffer solution for maintaining the test system within a pH range of about from 6.4 to 8.0 and at least one stabilizing compound capable of forming hydrogen bonds with the melamine;

B. determining the amount of color change due to the reaction between the melamine and the cyanuric acid; and, C. correlating the amount of color change to the concentration of cyanuring acid in the water.

12. A test method as in claim 11 wherein the stabilizing compound is selected from the group consisting of polyethylene glycol, ethylene glycol, glycerol, phenylarsene oxide, N-tris(hydroxymethyl)methyl-2-aminoethanesulfonic acid and mixtures thereof.

13. A test method as in claim 11 wherein the pH indicator material is selected from the group consisting of methyl red, phenol red, thymol blue, cresol red, metacresol purple, neutral red, curcumin, pyrocatecol and mixtures thereof.

14. A test method as in claim 11 wherein the pH of the test system is maintained within a range of about from 6.9 to 7.1.

15. A test method as in claims 11, 12, 13 or 14, wherein the test reagent system is a solution incorporated into a matrix material and dried prior to contact with the water sample.

16. The test reagent composition of claim 1, wherein the stabilizing compound is selected from the group consisting of polyalkylene glycols, alkylene glycols, non-polymeric polyalcohols, phenylarsene oxide, and N-tris(hydroxymethyl)methyl-2-aminoethanesulfonic acid.

* * * * *